United States Patent [19]

Incavo et al.

[11] Patent Number: 5,683,471
[45] Date of Patent: Nov. 4, 1997

[54] HYBRID TIBIAL TRAY KNEE PROSTHESIS

[76] Inventors: Stephen J. Incavo, 55 Butler Dr., South Burlington, Vt. 05403; James G. Howe, 8 Beaver Creek Rd., Shelburne, Vt. 05482

[21] Appl. No.: 527,111

[22] Filed: Sep. 12, 1995

Related U.S. Application Data

[62] Division of Ser. No. 252,892, Jun. 2, 1994, Pat. No. 5,480,444.

[51] Int. Cl.$^6$ ........................................ A61F 2/38
[52] U.S. Cl. .................................................. 623/20
[58] Field of Search ............................. 623/16, 18, 20

[56] References Cited

U.S. PATENT DOCUMENTS

| | | |
|---|---|---|
| 471,123 | 12/1892 | Brown . |
| 3,605,123 | 9/1971 | Hahn . |
| 3,855,638 | 12/1974 | Pilliar . |
| 3,866,248 | 2/1975 | Kummer . |
| 4,055,862 | 11/1977 | Farling . |
| 4,193,140 | 3/1980 | Treace . |
| 4,215,439 | 8/1980 | Gold . |
| 4,274,163 | 6/1981 | Malcolm . |
| 4,309,778 | 1/1982 | Buechel . |
| 4,358,859 | 11/1982 | Schurman . |
| 4,462,120 | 7/1984 | Rambert . |
| 4,470,158 | 9/1984 | Pappas . |
| 4,479,271 | 10/1984 | Bolesky . |
| 4,550,448 | 11/1985 | Kenna . |
| 4,551,863 | 11/1985 | Murray . |
| 4,593,685 | 6/1986 | McKay . |
| 4,881,536 | 11/1989 | Noble . |
| 4,938,769 | 7/1990 | Shaw . |
| 4,997,445 | 3/1991 | Hodorek . |
| 4,997,448 | 3/1991 | Filer . |
| 5,019,104 | 5/1991 | Whiteside . |
| 5,080,675 | 1/1992 | Lawes . |
| 5,171,276 | 12/1992 | Caspari . |
| 5,201,766 | 4/1993 | Georgette . |
| 5,236,462 | 8/1993 | Mikail . |
| 5,314,480 | 5/1994 | Elloy . |
| 5,326,359 | 7/1994 | Oudard . |

OTHER PUBLICATIONS

Load Transfer Characteristics of a Noncemented Total Knee Arthorplasty, Leo A. Whiteside, MD and John Pafford, BS, *Clin. Orthrop. and Rel. Res.*, 239:168–177, 1989.

Comparison of Magnetic Resonance Imaging and Lumbar Discography in the Diagnosis of Disc Degeneration, March A. Linson, M.D. and Christopher H. Crowe, M.D., *Clin. Orthrop. and Rel. Res.*, 250:160–163, 1990.

Fixation of Tibial Components of Knee Prostheses, P.S. Walker, PH.D., D. Greene, M.S., D. Reilly, PH.D., M.D., J. Thatcher, B.S., M. Ben–Dov., M.S.F., C. Ewald, M.D., *The Journal of Bone and Joint Surgery*, vol. 63–A, No. 2, Feb. 1981, 258–267.

Stability of Initial Fixation of the Tibial Component in Cementless Total Knee Arthroplasty, Hitoshi Shimagaki, Joan E. Bechtold, Robert E. Sherman, and Ramon B. Gustilo, *J. Orthop Res*, vol. 8, No. 1, 1990, 64–71.

Techniques In Orthopaedics, Shaw, James A., "Hybrid Fixation Modular Tibial Prosthesis", pp. 69–79, published Dec. 1991.

Will Stress Shielding Limit the Longevity of Cemented Femoral Components of Total Hip Replacement?, William H. Harris, M.D., *Clin. Orthop. and Rel. Res.*, 274:121–123.

(List continued on next page.)

*Primary Examiner*—Michael J. Milano
*Attorney, Agent, or Firm*—C. Dean Domingue; Robert L. Waddell

[57] ABSTRACT

A method for implanting a one-piece hybrid tibial tray component of a knee replacement prosthesis is disclosed. The method includes cutting an upper end of a tibia to accommodate the shape of the hybrid tibial tray and then punch fitting a tibial baseplate template having an imprint into the tibia. Next, cement is applied to the peripheral surface and the hybrid tibial tray is pressed down into the upper end of the tibia. Also, a temporary partition may be included, with the temporary barrier forming a barrier between the central area of the tibia and the peripheral area of the tibia.

2 Claims, 5 Drawing Sheets

OTHER PUBLICATIONS

The Case for Porous–Coated Hip Implants, Charles A. Engh, M.D., Andrew H. Glassman, M.D. and Kathleen E. Suthers, M.D., *Clin. Orthop. and Rel. Res.*, 261:63–81.

The Relationship Between Stress Shielding and Bone Resorption Around Total Hip Stems and the Effects of Flexible Materials; Rik Huiskes, Ph.D., Harrie Weinans, M.S. and Bert van Bietbergen, M.A., *Clin. Orthop. and Rel. Res.*, 274:124–134.

Four Screws for Fixation of the Tibial Component in Cementless Total Knee Arthroplasty; Leo A. Whiteside, M.D., *Clin. Orthop. and Rel. Res.*, 299:72–76.

Tibial Osteolysis in Cementless Total Knee Arthroplasty: A Review of 23 Tibial Lesions Surgically Treated With and Without Tibial Component Retention., *Presented at The Knee Society Scientific Meeting, New Orleans, LA*, Feb. 27, 1994, Gerard A. Engh, M.D., Nancy L. Smith, M.S., Deborah J. Ammeen, B.S.

Requirements for Successful Total Knee Replacements; Peter S. Walker, PhD, Orthrop., *Clin. of North Am.*, 20:15–29, 1989.

The Mechanical Stability of Various Noncemented Tibial Components; Robert G. Volz, M.D., Jon K. Nisbet, M.D., Russell W. Lee, M. Sc., and Michael G. McMurtry, B.S., *Clin. Orthop. and Rel. Res.*, 226:38–42, 1988.

The Role of Fixation and Bone Quality on the Mechanical Stability of Tibial Knee Components; Russell W. Lee, M.Sc., Robert G. Volz, M.A. and Donald C. Sheridan, M.D., *Clin. Orthop. and Rel. Res.*, 259:160–168, 1990.

Total Knee Arthroplasty; John N. Insall, M.D., Robierto Binazzi, M.S., Michael Soudry, M.D., and Luiz A. Mestriner, M.D., *Clin. Orthrop. and Rel. Res.*, 192:13–22, 1985.

Current Principles of Design for Cemented and Cementless Knees; David F. Bindelglass, M.D., Jondy L. Cohen, M.C. and Lawrence D. Dorr, M.S. *Techniques Orthop.*, 6:80–85, 1991.

Rigidity of Initial Fixation with Uncemented Tibial Knee Implants, Philip J. Branson, M.D., John W. Steege, MSME, Richard L. Wixson, M.D., Jack Lewis, PhD. and S. David Stulbert, M.D., *J. of Arthroplasty*, 4:21–26, 1989.

Stability and Anchorage Considerations for Cementless Tibial Components, A. J. Dempsey, MASc, J.B. Finlay, PhD, R.B. Bourne, MD FRCS(C), C.H. Rorabeck. MD, FRCS(C), M.A. Scott, BSc, and J.C. Millman, *The Journal of Arthroplasty*, vol. 4 No. 3 Sep. 1989.

HYBRID TIBIAL TRAY KNEE PROSTHESIS

This is a division of application Ser. No. 08/252,892 filed Jun. 2, 1994, now U.S. Pat. No. 5,480,444.

FIELD OF THE INVENTION

The present invention relates to an orthopedic prosthetic device and a method of implanting such device. More particularly, the present invention relates to a hybrid tibial tray component of a knee replacement prosthesis having a plate containing a peripheral surface for receiving bone cement and a central surface which promotes bone ingrowth.

BACKGROUND OF THE INVENTION

Arthritis of the knee joint is not only painful but can be permanently debilitating. With ever increasing frequency, doctors are replacing arthritic knees with prosthetic devices having a tibial, a femur and a patella component which mimic the articulation between the tibia and the femur. A complete knee replacement is often referred to as a Total Knee Arthroplasty (TKA). It is a primary goal of TKA to provide a stable, pain free and long lasting knee replacement.

There are traditionally two types of TKA. The first type involves mechanically linking the tibial and femur components of the prosthesis which is termed a "constrained" prothesis. In the second type, the tibial and femur components are not mechanically linked but rather are physiologically stabilized with a patient's muscle and ligaments. This prothesis type is commonly known as a "unconstrained" prothesis, and comprises the overwhelming majority of current knee replacements. It is not surprising, based on the popularity of knee replacement surgery, that the United States patent literature is replete with examples of both constrained and unconstrained knee replacement prothesis. For example, U.S. Pat. Nos. 4,358,859 and 4,462,120 are representative of constrained prothesis. U.S. Pat. Nos. 4,309, 778 and 4,470,158 are representative of unconstrained prothesis.

Fixation of the tibia, femur and patella components of the prothesis during implantation has customarily involved either bone cement or natural bone ingrowth. Orthopedic surgeons typically prefer cementless fixation for what is considered to be its potential to provide long term implant stability. Knee replacement prothesis wherein fixation is accomplished through bone ingrowth may have a porous layer to facilitate bone ingrowth. For instance, U.S. Pat. No. 4,479,271 discloses a tibial component which utilizes a fibrous metal mesh layer to facilitate bone ingrowth. U.S. Pat. Nos. 3,605,123; 3,855,638; and 4,550,448 further disclose porous layers which aid in the development of bone ingrowth.

Three factors are thought of as important for achieving optimal bone ingrowth: (1) close contact between bone and the prothesis, (2) the absence of micromotion and (3) the elimination of any effect which would inhibit bone growth. (see, Voltz, R. G.; Nisbet, J. K.; Lee, R. W.; and McMurtry, M. G.: The Mechanical Stability of Various Noncemented Tibial Components., *Clin. Orthop. and Rel. Res.*, 226:38–42, 1988). Loosening due to micromotion of the tibial component is the most frequent cause of long term TKA failure. Porous coated implant designs were thought to have solved the loosening problem by providing a stable implant fixation through bony ingrowth. (see, Shimakagi, H.; Bechtold, J. E.; Sherman, R. E.; and Gustilo, R. B.: Stability of the Tibial Component in Cementless Total Knee Arthroplasty., *J. of Orthopaedic Res.*, 8:64–71, 1990). However, cancellous bone ingrowth in the tibial prosthesis has been unpredictable. (see, Branson, P. J.; Steege, J. W.; Wixson, R. L.; Lewis, J.; and Stulberg, S. D.: Rigidity of Initial Fixation with Uncemented Tibial Knee Implants., *J. of Arthroplasty*, 4:21–26, 1989; Miura, H.; Whiteside, L. A.; Easley, J. C.; and Amador, D. D.: Effect of Screws and a Sleeve on Initial Fixation in Uncemented Total Knee Tibial Components., *Clin. Orthop. and Rel. Res.*, 259:160–168, 1990; and Voltz, R. G.; Nisbet, J. K.; Lee, R. W.; and McMurtry, M. G.: The Mechanical Stability of Various Noncemented Tibial Components., *Clin. Orthop. and Rel. Res.*, 226:38–42, 1988).

Testing of different tibial configurations, such as peripherally placed cancellous screws, sleeves, central stems and pegs, has shown that some resistance to micromotion can be obtained. (see, Branson, P. J.; Steege, J. W.; Wixson, R. L.; Lewis, J.; and Stulberg, S. D.: Rigidity of Initial Fixation with Uncemented Tibial Knee Implants., *J. of Arthroplasty*, 4:21–26, 1989; Cameron, H. U.: Noncemented Tibial Components: Does a Stem Help?, *Contemporary Orthopaedics*, 24:326–330, 1992; Lee, R. W.; Voltz, R. G.; and Sheridan. D. C.: The Role of Fixation and Bone Quality on the Mechanical Stability of Tibial Knee Components., *Clin. Orthop. and Re. Res.*, 259:160–168, 1990; Miura, H.; Whiteside, L. A.; Easley, J. C.; and Amador, D. D.: Effect of Screws and a Sleeve on Initial Fixation in Uncemented Total Knee Tibial Components., *Clin. Orthop. and Rel. Res.*, 259:160–168, 1990; Shimakagi, H.; Bechtold, J. E.; Sherman, R. E.; and Gustilo, R. B.: Stability of the Tibial Component in Cementless Total Knee Arthroplasty., *J. of Orthopaedic Res.*, 8:64–71, 1990; and Voltz, R. G.; Nisbet, J. K.; Lee, R. W.; and McMurtry, M. G.: The Mechanical Stability of Various Noncemented Tibial Components., *Clin. Orthop. and Rel. Res.*, 226:38–42, 1988). The reason for inconsistent results with ingrowth stems from the inability for implant designs to provide adequate initial fixation in order for bone growth to occur. (see, Bindeglass, D. F.; Cohen, J. L.; and Doff, L. D.: Current Principles of Design for Cemented and Cementless Knees., *Techniques Orthop.*, 6:80–85, 1991; and Miura, H.; Whiteside, L. A.; Easley, J. C.; and Amador, D. D.: Effect of Screws and a Sleeve on Initial Fixation in Uncemented Total Knee Tibial Components., *Clin. Orthop. and Rel. Res.*, 259:160–168, 1990).

Cemented TKA prosthesis designs have met with more clinical success and a lower incidence of loosening due to micromotion. (see, Krackow, K. A.; Hungeford, D. S.; Trnka, H. J.; Maar, D. C.; Mont, M. A.; and Urquhart, M.: Cemented Versus Uncemented Primary Total Knee Arthroplasty: A Comparative Study of the First 100 Patients in Each Group., *Read at the Annual Meeting of the American Academy of Orthopaedic Surgeons, Washington D.C.*, Feb. 20, 1992; Insall, J. N.; Binazzi, R.; Soudry, M.; and Mestfiner, L. A.: Total Knee Arthroplasty., *Clin. Orthrop. and Rel. Res.*, 192:13–22, 1985; and Walker, P. S.: Requirements for Successful Total Knee Replacements, Orthrop., *Clin. of North Am.*, 20:15–29, 1989). Yet, even bone cement fixated prosthetic components are susceptible to loosening.

Hybrid knee replacement prosthetic components have been developed in an attempt to overcome some of the above described disadvantages of the cementless and bone cement prosthesis. Hybrid components utilize both cement and bone ingrowth for fixation. An example of such a hybrid tibial component is disclosed in U.S. Pat. No. 4,938,769 to Shaw. The Shaw patent teaches a removable tibial tray component having a bone anchorage assembly including a central stem and two pegs. The central stem is designed to fit within the intramedullary canal, and the pegs, which are spaced symmetrically from the central stem, are structured to fit within the posterior-lateral and posterior-medial quadrants of the tibia. The central stem and pegs may contain an area coated with a porous metal to promote bone ingrowth. The Shaw patent further teaches that the distal end of the tibial tray may have a narrow, axially raised flange positioned on its periphery. The flange provides an area for the application of bone cement when the tibial tray is positioned on the tibia. In a preferred embodiment, the distal side of the tibial tray has one or more walled recesses which may be angled acutely and which serve to fixate the tibial tray to the tibia through the use of bone cement. The Shaw patent teaches that immediate fixation via the bone cement encourages permanent fixation of the prosthesis via bone ingrowth by minimizing motion between the bone surface and the prosthesis.

The Shaw tibial prosthesis suffers from disadvantages primarily resulting from the placement of the porous bone ingrowth material on the central stem and pegs. The central stem and pegs of the Shaw prosthesis are structured to fit within the tibia itself and promote bone ingrowth between the bone tissue of the interior of the tibia and the central stem and pegs. While this design would appear to effectively promote bone ingrowth, because bone ingrowth occurs about the central stem and pegs, removal of the tibial prosthesis (as a result of infection) would cause excessive tibia damage. Moreover, the bone ingrowth area is of limited surface area and does not effectively utilize the larger surface area of the upper end of the tibia for bone ingrowth.

In addition, if bone ingrowth occurs on the stem as designed, physiologic loading of the proximal tibia may no longer occur. (Normally, the proximal tibia transmits all the forces placed on the leg.) Bone ingrowth occurring at a point from the proximal tibia surface can have the effect of bypassing the normal stress transfer of the tibia and lead to a situation of "stress-shielding" the proximal tibia surface. This phenomenon is well described in femoral prostheses used in hip replacements which obtain bone ingrowth in the femoral canal a distance away from the proximal femur (see Engh, Charles A.; Glassman, Andrew H.; and Suthers, Kathleen E.: The Case for Porous-Coated Hip Implants., *Clin. Orthrop. and Rel. Res.*, 261:63–81, 1990; Harris, William H.: Will Stress Shielding Limit the Longevity of Cemented Femoral Components of Total Hip Replacement, *Clin. Orthrop. and Rel. Res.*, 274:120–123, 1992; and Huiskes, Rik.; Weinans, Harrie.; and Van Rietbergen, Bert.: The Relationship Between Stress Shielding and Bone Resorption Around Total Hip Stems and the Effects of Flexible Materials., *Clin. Orthrop. and Rel. Res.*, 274:124–134, 1992). Although proponents of this prosthetic design consider this acceptable (albeit a less than optimal situation), most surgeons avoid this design because of possible long term deleterious effects such as severe weakening of the proximal bone leading to fractures around the prosthesis.

Finally, a most concerning problem of the two piece design of Shaw arises from the locking screws. The Shaw design assumes that both permanent cement fixation and bone ingrowth will occur every time the device is implanted. If bone ingrowth occurs on the stem and the cement suffers loss of fixation (either by stress-shielding described previously or by the usual slower cement loosening process) then a situation exists whereby the two piece design will be greatly stressed. The proximal plate can toggle on the well-fixed stem leading to problems with metallic wear debris from the opposing two surfaces and from the locking screws. Metallic wear debris from screws used to secure cementless tibial trays and cementless acetabular hip prostheses has been previously documented. (see Engh, Gerard A.; Smith, Nancy L.; and Ammeen, Deborah J.: Tibial Osteolysis in Cementless Total Knee Arthroplasty: A Review of 23 Tibial Lesions Surgically Treated With And Without Tibial Component Retention., *Presented at The Knee Society Scientific Meeting, New Orleans, La.*, Feb. 27, 1994; and Whiteside, Leo A.; Four Screws for Fixation of the Tibial Component in Cementless Total Knee Arthroplasty., *Clinical Orthrop. and Rel. Res.*, 299:72–76, 1994).

SUMMARY OF THE INVENTION

The present invention provides an improved hybrid tibial tray component of a knee replacement prosthesis. The tibial tray of the present invention includes a laterally extending plate that is shaped to fit the patient's tibia as part of a knee replacement surgical procedure.

The plate has a distal surface (undersurface) comprising a peripheral surface for receiving bone cement and a central surface which promotes bone ingrowth. A central stem extends from the distal surface of the plate.

The plate may also have a partition which may be a raised shoulder generally V-shaped in cross section which serves to separate the central surface from the peripheral surface. Alternatively, the partition may be a stepped portion containing the central surface which is then in a raised position relative to the peripheral surface. The partition is designed to prevent the flow of bone cement from the peripheral surface to the central surface.

The hybrid tibial tray of the present invention is a one-piece design. The one-piece hybrid tibial tray allows for close contact between bone and prosthesis. Bone ingrowth occurs between the upper end of the tibia (a large surface area) and the undersurface of the tibial tray and not in the central stem area within the interior of the tibia. The tibial tray can thus be removed with relative ease and without substantial damage to the tibia. In addition, the one-piece design alleviates problems common to a two piece tibial tray, such as toggling which may cause debris to be formed.

The present invention is also directed to an unique method for implanting the above described one-piece hybrid tibial tray. The method involves cutting the end of the upper tibia of a patient in a shape to accommodate to hybrid tibia tray. A tibial base plate template which has an imprint of the partition is punch fit into the end of the tibia to form in the tibia a slot to receive the partition. Cement is then applied to the peripheral surface of the plate, and the plate is placed on the upper end of the tibia for fixation. Alternatively, a temporary partition may be placed in the slot formed in the tibia and bone cement placed in the area surrounding the partition to which the peripheral surface of the plate will attach. The partition is then removed and the hybrid tibial tray fixed on the upper end of the tibia.

DETAILED DESCRIPTION OF THE PREFERRED EMBODIMENTS

With reference to the figures where like elements have been given like numerical designation to facilitate an understanding of the present invention, and particularly with reference to the embodiment of the one-piece hybrid tibial tray of the present invention illustrated in FIGS. 1-4, the hybrid tibial tray 10 may include a laterally extending plate 11. Plate 11 is preferably shaped to fit the upper end of a patient's tibia. It is especially preferred if plate 11 has a height in the range of 3.0 to 7.0 mm.

Figure 1:
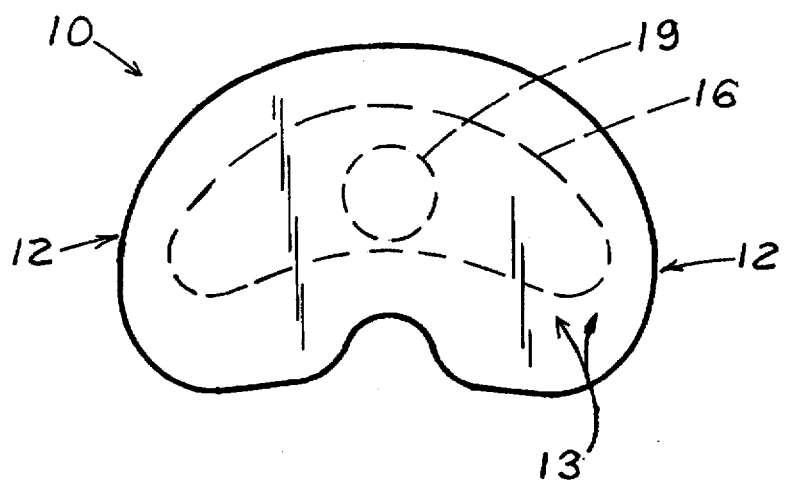
FIG. 1 is a top view of a first embodiment of the tibial tray.
Figure 3:
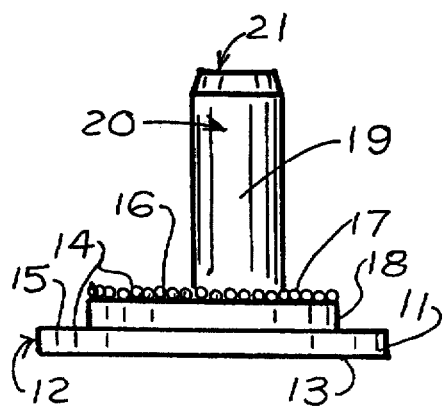
FIG. 3 is a side view of the first embodiment of the tibial tray taken along lines 3—3 of FIG. 2.

As shown in FIGS. 1 and 3, plate 11 may have a peripheral shoulder 12. Preferably, plate 11 has a width of 80 mm. and a length of 53 mm. Plate 11 may also have a proximal surface 13 that receives the femur component of the knee replacement prosthesis. It is preferred that proximal surface 13 be generally flat.

Figure 2:
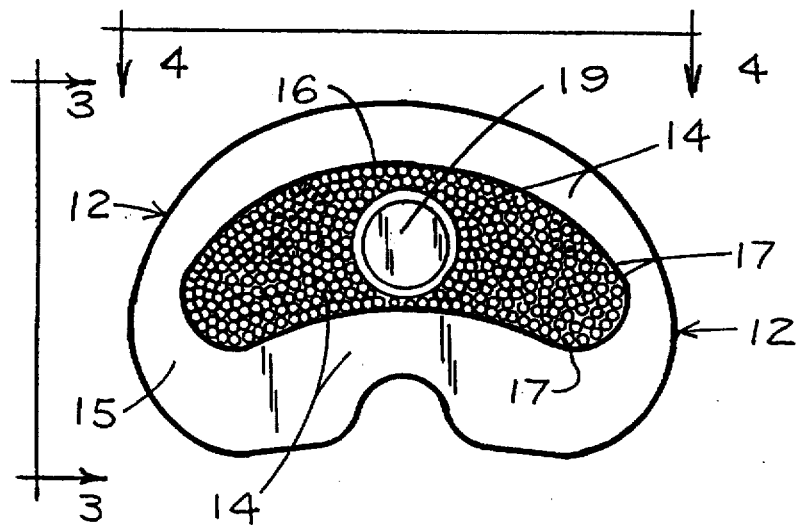
FIG. 2 is a bottom view of the first embodiment of the tibial tray.
Figure 6:
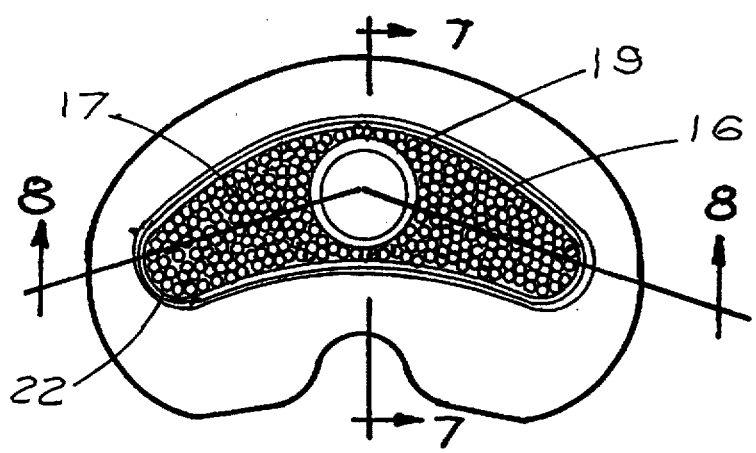
FIG. 6 is a bottom view of the second embodiment of the tibial tray.

With reference to FIGS. 2 and 6, plate 11 may have a distal surface 14 which is intended to be placed against the upper end of a patient's tibia and fixed thereto during implantation of hybrid tibial tray 10. Distal surface 14 preferably includes a peripheral surface 15 for receiving bone cement and a central surface 16 which promotes bone ingrowth.

It is desirable if peripheral surface 15 has a diameter of 7 mm. at the front side of hybrid tibial tray 10, 12 mm. at the rear side of hybrid tibial tray 10, and 8 mm. at each of the sides of hybrid tibial tray 10. Peripheral surface 15 receives bone cement upon implantation of hybrid tibial tray 10 and affords close apposition between the tibial cancellous bone and central surface 16. Bone cement at and around peripheral surface 15 of hybrid tibial tray 10 permits rigid fixation equal to that of traditional cement prothesis. The use of bone cement at peripheral surface 15 aids the ingrowth process by providing a more even surface for the normal axial loading of the tibia to be distributed. Even distribution of force is material to the reduction of micromotion and the success of bone ingrowth in central surface 16 of hybrid tibial tray 10.

Central surface 16 preferably is made of material which promotes bone ingrowth. For example, central surface 16 may be a porous material or have a surface layer of porous material which promotes bone ingrowth. An example of such material is a fibrous metal mesh such as that taught in U.S. Pat. No. 4,479,271, the disclosure of which is incorporated herein by reference.

More preferably, central surface 16 may be coated with a bone ingrowth promoting material. The coating preferably forms a porous layer 17. Examples of such porous layers are found in U.S. Pat. Nos. 3,605,123; 3,855,638; 4,550,448; and 5,201,766, the disclosures of which are incorporated herein by reference. It is especially preferred if the porous layer 17 is composed of a plurality of metallic beads. Such beads are well known and are commercially available. Porous layer 17 deskably has a thickness in the range of 0.5 to 2.0 mm.

As illustrated in FIGS. 3, 4, 7 and 8, hybrid tibial tray 10 may have a central stem 19 extending from distal surface 14 of plate 11. Central stem 19 is designed to fit within intramedullary canal of a patient's tibia when implanted. Preferably, central stem 19 has a cylindrically shaped side wall 20 and a circular distal end 21. Side wall 20 of central stem 19 may be uniform in diameter or tapered toward distal end 21. Central stem 19 further aids in reducing micromotion and thus contributes to successful bone ingrowth. Plate 11 and central stem 19 may be constructed of a biocompatible material such as medical grade titanium.

Figure 7:
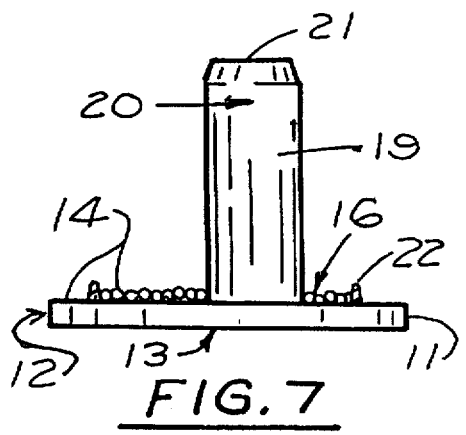
FIG. 7 is a side view of the second embodiment of the tibial tray taken along lines 7—7 of FIG. 6.
Figure 8:
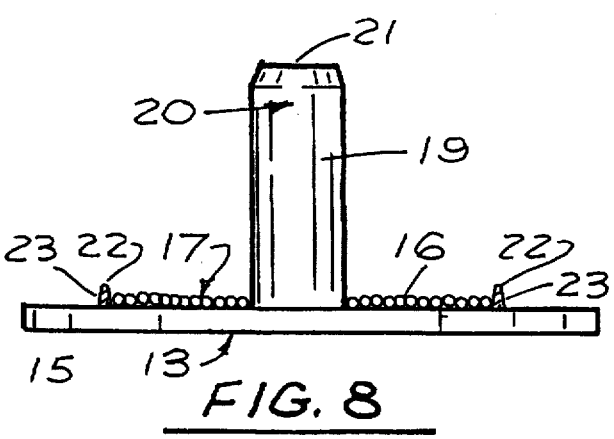
FIG. 8 is a side view of the second embodiment of the tibial tray taken along lines 8—8 of FIG. 6.

With reference to FIGS. 7 and 8, plate 11 may have a partition separating peripheral surface 15 from central surface 16. Preferably, the partition is a continuous structure, for example, a raised shoulder 22 which may completely surround central surface 16. It is especially desirably if raised shoulder 22 is configured as shown in FIG. 7 and 8, with a V-shaped cross section 23 and having a height which is at least the height of porous layer 17. More preferably, raised shoulder 22 is of a height which is greater than the height of porous layer 17. It is also preferable for the height of raised shoulder 22 to be twice the height of plate 11. For example, raised shoulder 28 may have a height in the range of 0.6 to 2.1 mm or in the range of 6.0 to 14.0 mm.

Figure 4:
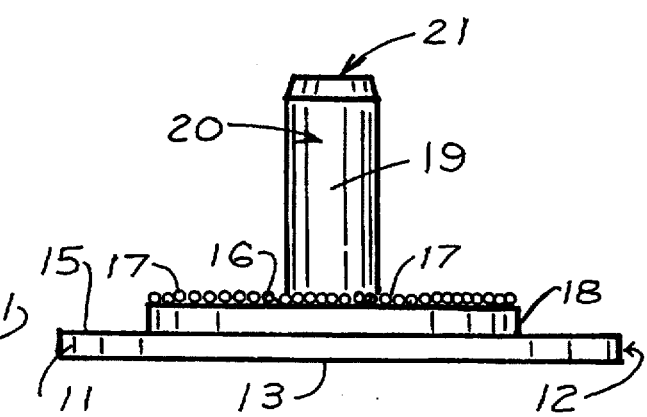
FIG. 4 is a front view of the first embodiment of the tibial tray taken along lines 4—4 of FIG. 2.
Figure 5:
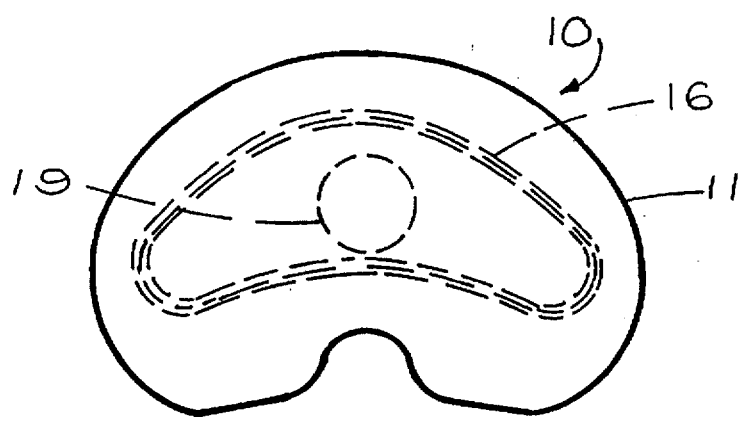
FIG. 5 is a top view of a second embodiment of the tibial tray.

Referring now to FIGS. 3 and 4, the partition may be in the form of stepped portion 18 containing central surface 16. In this configuration, central surface 16 is raised in relation to peripheral surface 15. It is preferred if stepped portion 18 has a height that is twice the height of plate 11. For example, stepped portion 18 may have a height in the range of 3.0 to 14.0 mm. or more preferably in the range of 3.0 to 8.0 mm. A height of 6.0 mm. is most preferred.

The surface area of the peripheral surface 15 and the surface area of central surface 16 are, in a preferred embodiment, substantially equal.

Figure 9:
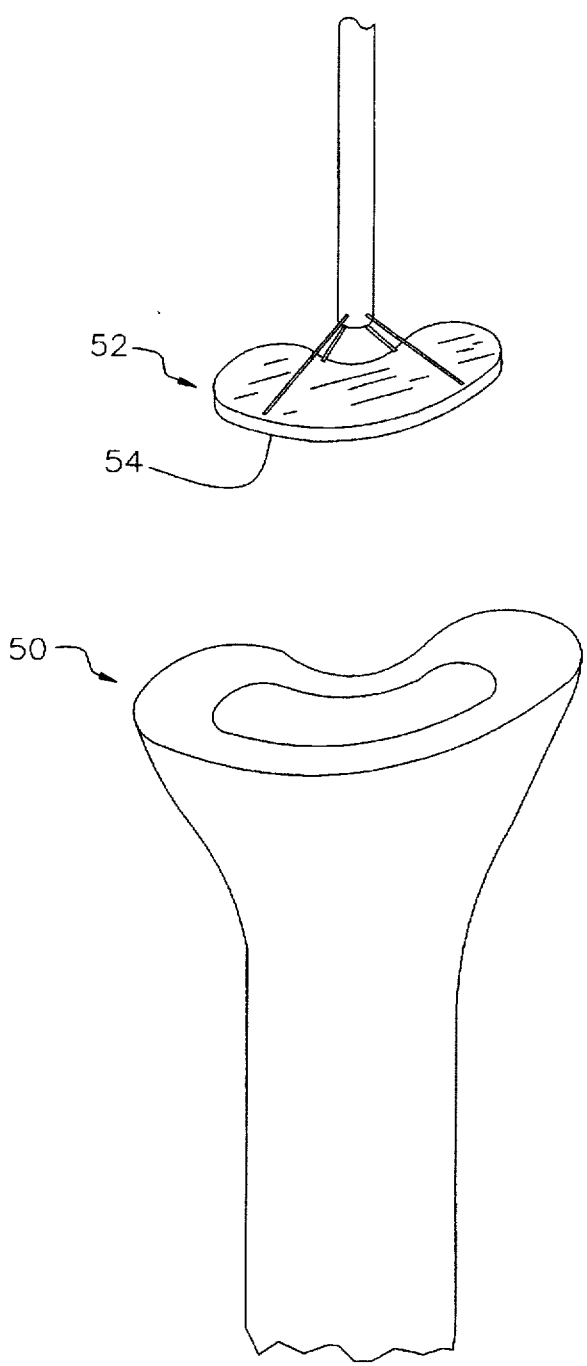
FIG. 9 is a perspective view of the cut tibial surface and the tibial baseplate template positioned above.
Figure 10:
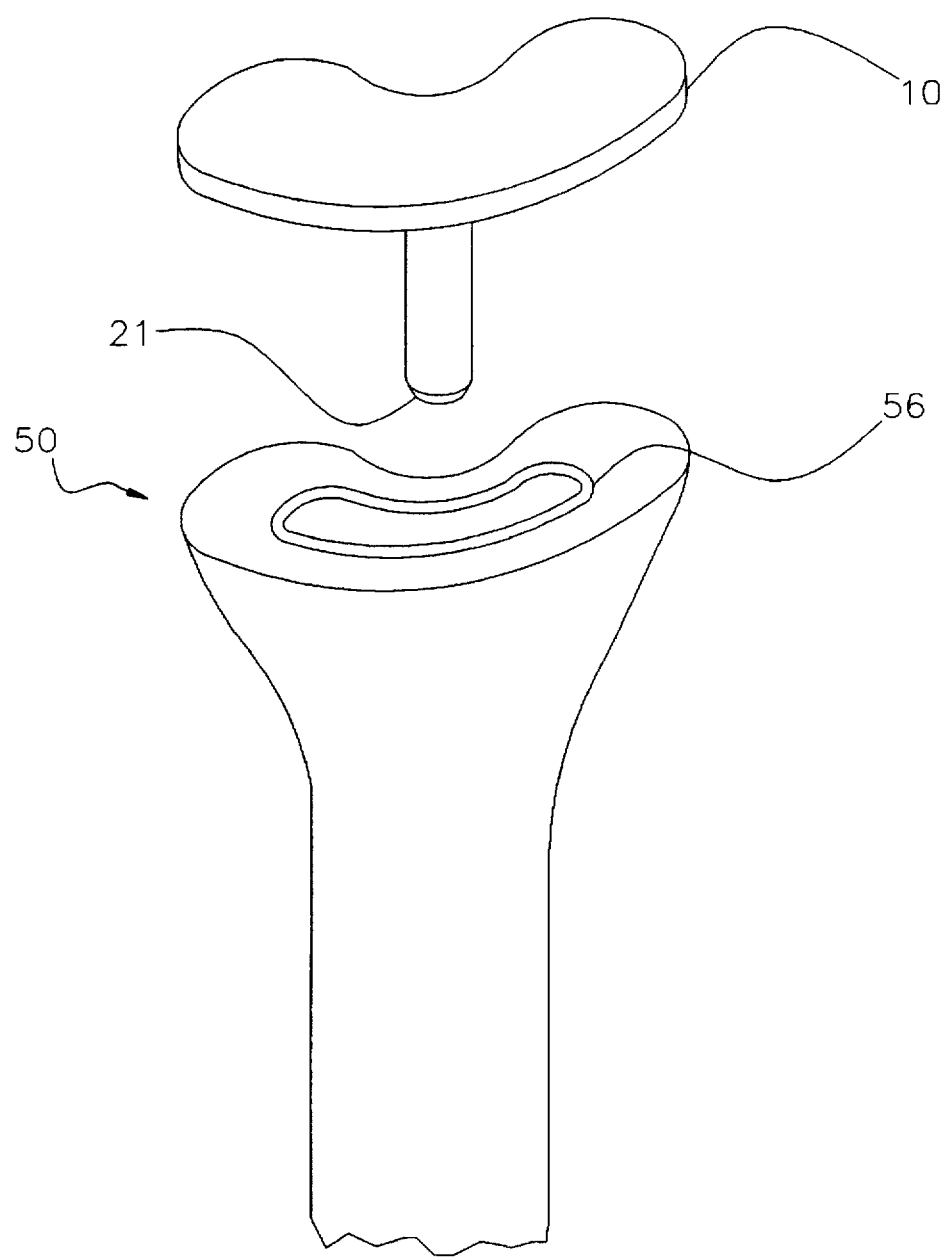
FIG. 10 illustrates the tibial tray with fence removed so that the hybrid tibial tray may be pressed down into the upper end of the tibia surface.
Figure 11:
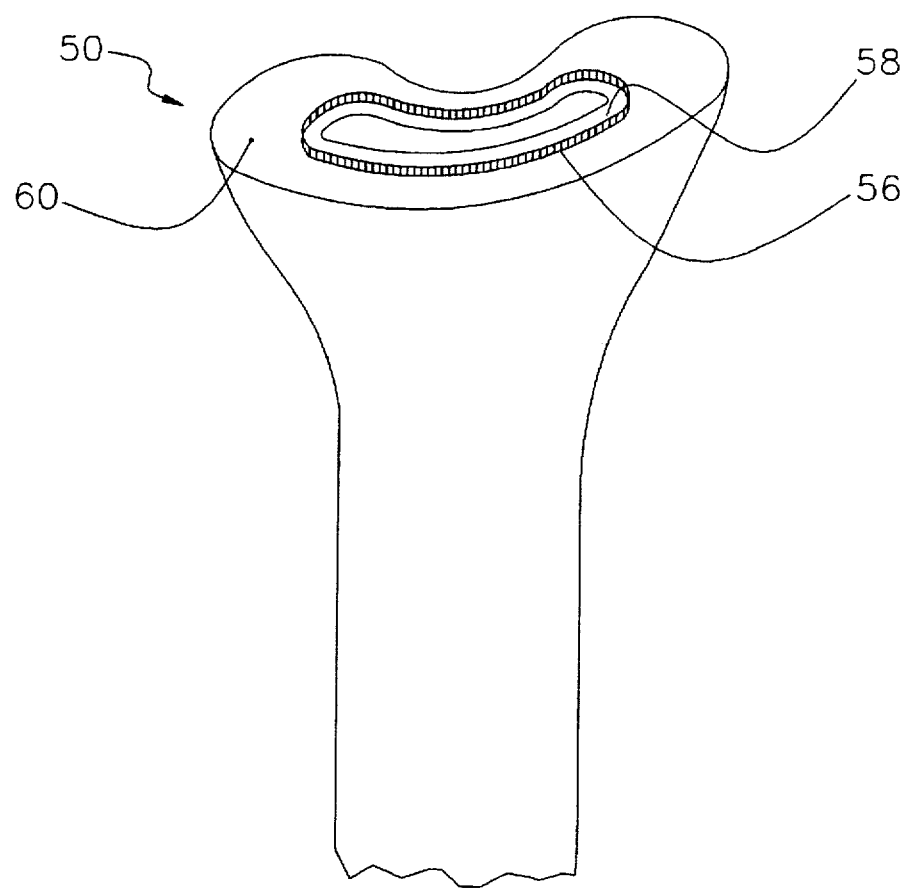
FIG. 11 depicts the temporary partition placed on said tibial surface.

As seen generally in FIG. 9 implanting hybrid tibial tray 10 in the tibia of a patient is accomplished by first cutting the end of the upper tibia 50 in a shape to accommodate hybrid tibial tray 10. A tibial base plate template 52 which has an imprint 54 of the partition is punch fit into the end of the tibia to form, in the tibia, a slot 56 to receive the partition such as raised shoulder 22. Cement is then applied to the peripheral surface 15 of plate 11 of hybrid tibial tray 10. Hybrid tibial tray 10 is then pressed down into the upper end of the tibia so that peripheral surface 15 rests against the tibia and central surface 16 and the partition (either stepped portion 18 or raised shoulder 22) is implanted within the tibia bone tissue for fixation to the tibia, as shown in FIG. 10. In an alternative method shown in FIG. 11, a temporary partition 58, such as a raised shoulder, may be placed in the slot 56 formed in the tibia. Bone cement is then placed in the area surrounding the partition to which peripheral surface 15 of the plate 11 will attach. The partition 58 is then removed and hybrid tibial tray 10 fixed on the upper end of the tibia as aforementioned.

The following example present results of laboratory tests conducted comparing the hybrid tibial tray of the present invention with standard modes of prosthetic fixation such as cement, cancellous screws, central stem and cementless.

EXAMPLE

A uniform density polyurethane foam was used as a substrate for this study, Last-A-Foam (Pacific Plastics Research Laboratories, Vashon Island, Wash.). Its material properties are similar to tibial cancellous bone, and its use is well documented. The foam was machined into uniform blocks and each block was fitted to a testing jib to prevent variability between testing sequences and eliminate background motion artifact.

The testing jig consisted of liquid mercury strain gauges (LMSG, Parks Medical Electronics, Beaverton, Oreg.) attached to transitable arms (X,Y,Z) for alignment with the tibial tray. Each LMSG was attached to a translatable arm and attached to the tibial tray. Four LMSGs were used per tray fixed to the anterior, posterior, medial, and lateral regions of the tray. The LMSG records a voltage change due to movement of the tray. Calibration curves for each LMSG allow extrapolation of the movement in micrometers. Calibration curves were obtained by opening the gauge in fixed metric increments and recording the voltage at these increments.

The traditional noncemented trays had a 30 mm central stem. For implantation into the foam a hole was drilled, slightly smaller than the stem, to fix the prosthesis to the foam. The noncemented design with screws had two ¼" drill holes made in the foam for fixation of the 6.5 mm cancellous screws. In addition to the central hole drilled as in the traditional noncemented. The noncemented with a long stem, had a hole drilled to accommodate the longer stem. The traditional cemented was implanted using surgical cement with 1/16" drill holes made in the surface of the foam to mimic the operative situation and increase stability. The hybrid noncemented was fit to the block by machining an area for the undersurface to sit in the foam. The hybrid cemented also had a machined area for the undersurface. In addition, 1/16" drill holes were made around the periphery where the cement was placed to aid in stability.

Tibial baseplates were fitted to the foam blocks with their respective modes of fixation and then centrally loaded with 150 lb. This load stabilized the tray in the foam for testing purposes. Once the tray was fixed to the foam in its respective manner it was put through the testing sequence. All specimens were loaded on a Materials Testing System (MTS Systems Corporation, Minneapolis, Minn.). Each loading trial consisted of five loads (100 lbs.–500 lbs.) in 100 pound increments, placed in one of five positions (anterior, posterior, medial, lateral, central). After each of the five loads was applied in the positions, the specimen was removed from the foam and fixed to a new block of foam. At the loading intervals, the voltage of all four LMSGs was recorded simultaneously. The load was applied, allowed to stabilize, and then sampling of the LMSGs occurred for five seconds at five hertz. This gave twenty-five data points per gauge per loading interval. These twenty-five points were averaged for each LMSG. In all trials the load was applied in a uniform axial manner, parallel to the tibia.

Each method of fixation was tested in six different blocks of foam consecutively. After all six trials were complete, the data was averaged for that method of fixation and compared to the others. Therefore, there were thirty-six blocks of foam tested in all, six configurations for six trials each. For each trial, one per foam block, a data file was created that contained the displacement of each gauge per loading situation. This allowed the comparison of all designs at all loading configurations.

Tray configurations were analyzed by an analysis of variance using a standard T-test and Tukey's studentized range (HSD) test. All configurations consisted of a Richards Genesis large right tibial component (Richards Medical Co., Memphis, Tenn.). The same noncemented component was used repeatedly depending on the configuration. The cemented component was used for the cemented applications only. Howmedica Simplex-P Radiopaque Bone Cement (Howmedica Inc. Rutherford, N.J.) was used for all trials of the cemented and the hybrid cemented. No cement centrifugation or vacuum mixing was employed.

The hybrid configuration consisted of a noncemented baseplate with a smaller 6 mm block placed on the undersurface of the tray. This provided a 5 mm rim for cement application but allowed for central ingrowth. The block was held in place through screws affixed to the plate.

In total six configurations were tested: (1) traditional cemented; (2) hybrid cemented; (3) noncemented with no additional fixation; (4) noncemented with central stem; (5) noncemented with two 6.5 mm cancellous screws; (6) hybrid noncemented.

The greatest amount of micromotion was detected at 500 pounds. The greatest micromotion (subsidence) occurred at the point of load application, except in the case of central loading which showed maximum subsidence anteriorly. Mean values for motion at 500 pounds are given in Table 1.

The largest subsidence values were recorded for the anterior load. At 500 pounds the values ranged from 0.407 mm to 0.724 mm (Table 1). Analysis of variance demonstrated three statistically distinct groups: (1) Hybrid cemented (N=36, DOF Model=5, DOF Corrected=35, p=0.0001, F=26.85, $\alpha$=0.05, $r^2$=0.817); (2) Traditional cemented and noncemented with stem; and (3) the remaining three configurations.

Smaller values for subsidence was seen in the posterior load testing mode (range 0.192 mm to 0.366 mm)(Table 1). Analysis of variance demonstrated two statistically significant groups: (1) Hybrid cemented and (2) all other groups (N=36, DOF Model=5, DOF Corrected=35, p=0.0001, F=35.52, $\alpha$=0.05, $r^2$=0.855).

Subsidence values ranged from 0.213 mm to 0.413 mm for this testing mode (Table 1). Statistically, two separate groups were superior by analysis of variance: (1) Traditional cemented and hybrid cemented, and (2) all other designs (N=36, DOF Model=5, DOF Corrected=35, p=0.0014, F=5.26, $\alpha$=0.05, $r^2$=0.467).

In this lateral load testing mode, the values ranged from 0.288 mm to 0.487 mm (Table 1). Three statistically separate groups were identified by analysis of variance: (1) Traditional cemented and Hybrid cemented (N=36, DOF Model=5, DOF Corrected=35, p=0.0001, F=7.48, $\alpha$=0.05, $r'$=0.555); (2) Hybrid noncemented (p<0.001): (3) the three remaining configurations.

Subsidence values ranged from 0.234 mm to 0.446 mm for central Loading (Table 1). Analysis of variance identified two statistically different groups: (1) Traditional cemented and Hybrid cemented (N=36, DOF Model=5, DOF Corrected=35, p=0.0001, F=23.52, $\alpha$=0.05, $r^2$=0.798) and (2) the remaining four configurations.

The results of the test indicate that the hybrid tibial tray of the present invention provided equal and in some cases better initial fixation then the cemented design. In in vivo, the tibial tray of the present invention, with central ingrowth, would exhibit enhanced stability. Central bony ingrowth would account for long term stability of the prosthesis. The hybrid design permits a large undersurface area for ingrowth in addition to the use of cement for initial fixation.

TABLE 1*

| | Medial Load | Lateral Load | Anterior Load | Posterior Load | Central Load |
|---|---|---|---|---|---|
| Traditional Cemented | .213 | .288 | .497 | .231 | .274 |
| Hybrid Cemented | .262 | .328 | .407 | .192 | .234 |
| Cementless with Stem | .385 | .411 | .497 | .312 | .373 |
| Cementless with Screws | .394 | .437 | .688 | .326 | .412 |
| Traditional Cementless | .419 | .487 | .703 | .336 | .411 |
| Hybrid Cementless | .431 | .384 | .724 | .366 | .446 |

*Micromotion of different tray configurations. Mean values (mm) are reported at 500 lbs.

While preferred embodiments of the present invention have been described, it is to understood that the embodiments described are illustrative only and that the scope of the invention is to be defined solely by the appended claims when accorded a full range of equivalence, many variations and modifications naturally occurring to those skilled in the art from a perusal hereof.

What is claimed is:

1. A method for implanting a one-piece hybrid tibial tray component of a knee replacement prosthesis having a bone ingrowth surface that does not require separate attachment, comprising the steps of:

cutting an upper end of a tibia of a patient in a shape to accommodate a shape of a hybrid tibial tray comprising a laterally extending plate having a proximal surface and a distal surface, said distal surface including a peripheral surface for receiving bone cement and a planar central surface which promotes bone ingrowth, said peripheral surface and said planar central surface each having surface areas which are substantially equal; a raised shoulder continuously extending around said planar central surface which separates said peripheral surface from said planar central surface to prevent bone cement from flowing into said planar central surface, said raised shoulder having a V-shaped cross section; and a central stem extending from said distal surface and being perpendicular thereto;

punch fitting a tibial baseplate template having an imprint of said raised shoulder into the end of said tibia to form therein a slot to receive said raised shoulder;

applying cement to said peripheral surface; and pressing said hybrid tibial tray down into said upper end of the tibia so that said peripheral surface rests against said upper end and said planar central surface and said raised shoulder are implanted within bone tissue of said upper end of the tibia for fixation thereto.

2. A method for implanting a one-piece hybrid tibial tray component of a knee replacement prosthesis having a bone ingrowth surface that does not require separate attachment, comprising the steps of:

cutting an upper end of a tibia of a patient in a shape to accommodate a shape of a hybrid tibial tray comprising a laterally extending plate having a proximal surface and a distal surface, said distal surface including a peripheral surface for receiving bone cement and a planar central surface which promotes bone ingrowth; a raised shoulder continuously extending around said planar central surface which separates said peripheral surface from said planar central surface to prevent bone cement from flowing into said planar central surface, said raised shoulder having a V-shaped cross section; and a central stem extending from said distal surface and being perpendicular thereto;

punch fitting a tibial baseplate template having an imprint of said raised shoulder into the end of said tibia to form therein a slot to receive said raised shoulder;

placing a temporary partition in said slot to form a barrier between a central area of said upper end which is to receive said planar central surface of the tibial tray and a peripheral area of said upper end of the tibia which is to receive said peripheral surface of the tibial tray;

applying cement to said peripheral surface of said upper end of the tibia;

removing said temporary partition;

pressing said hybrid tibial tray down into said upper end of the tibia so that said peripheral surface rests against said upper end and said planar central surface and said raised shoulder are implanted within bone tissue of said upper end of the tibia for fixation thereto.

* * * * *

UNITED STATES PATENT AND TRADEMARK OFFICE
CERTIFICATE OF CORRECTION

PATENT NO. : 5,683,471
DATED : November 4, 1997
INVENTOR(S) : Stephen J. Incavo, James G. Howe It is certified that error appears in the above-identified patent and that said Letters Patent is hereby corrected as shown below:

On the title page, Item [75], Inventors. insert:

--Abraham Salehi, 3127 Sycamore, Memphis, TN 38134--

Signed and Sealed this

Fifteenth Day of September, 1998

*Attest:*

BRUCE LEHMAN

*Attesting Officer*     *Commissioner of Patents and Trademarks*